(12) United States Patent
Shen et al.

(10) Patent No.: US 8,691,590 B2
(45) Date of Patent: Apr. 8, 2014

(54) METHOD FOR EVALUATING EXTRINSIC HYDROGENATION DEGRADATION OF HYDROGEN STORAGE MATERIAL

(75) Inventors: Chia-Chieh Shen, Hsinchu (TW); Tsong-Pyng Perng, Hsinchu (TW); Hsueh-Chih Li, Jhongli (TW)

(73) Assignee: Yuan Ze University, Jhongli, Taoyuan County (TW)

( * ) Notice: Subject to any disclaimer, the term of this patent is extended or adjusted under 35 U.S.C. 154(b) by 304 days.

(21) Appl. No.: 13/038,904

(22) Filed: Mar. 2, 2011

(65) Prior Publication Data

US 2012/0225009 A1    Sep. 6, 2012

(51) Int. Cl.
*G01N 33/00*    (2006.01)
(52) U.S. Cl.
USPC .................. 436/144; 423/645; 423/648.1
(58) Field of Classification Search
None
See application file for complete search history.

(56) References Cited

PUBLICATIONS

Dillon et al. "Carbon Nanotube Materials for Hydrogen Storage", Proceedings of the 2001 DOE Hydrogen Program Review, no page numbering, total 17 pages.*
Park and Lee "The intrinsic degradation phenomena of LaNi5 and LaNi4.7Al0.3 by temperature induced hydrogen absorption-desorption cycling", Materials Research Bulletin, 1987, v. 22, No. 4, pp. 455-465, Abstract.*
Broom reviews "Hydrogen Sorption Measurements on Potential Storage Materials", JRC Scientific and Technical Reports, European Commission, 2008, Luxemburg, total 86 pages.*
Liu et al. "Intrinsic/Extrinsic Degradation of Ti-V-Based Hydrogen Storage Electrode Alloys upon Cycling", J. Phys., Chem., 2008, v. 112, pp. 16682-16690.*

* cited by examiner

*Primary Examiner* — Yelena G Gakh
(74) *Attorney, Agent, or Firm* — Egbert Law Offices, PLLC

(57) ABSTRACT

A hydrogen storage material analyzer along with its analysis and activation methods, the hydrogen storage material analyzer including a $H_2$ absorption-desorption cycling tester, a temperature-programmed desorption spectrometer, a specimen holder and a temperature-controlled furnace.

2 Claims, 12 Drawing Sheets

(a)

(b)

METHOD FOR EVALUATING EXTRINSIC HYDROGENATION DEGRADATION OF HYDROGEN STORAGE MATERIAL

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates generally to a hydrogen storage material analyzer, and more particularly to an innovative one which involves hydrogenation degradation analysis and activation methods.

2. Description of Related Art Including Information Disclosed Under 37 CFR 1.97 and 37 CFR 1.98.

Hydrogen technology is extensively applied in the fields of the syntheses of methanol and ammonia, hydrogen engine, hydrogen fuel cell and fossil industries. Hydrogen fuel cells are characterized by higher operating efficiency and zero pollution.

Due to the advantages of hydrogen technologies, the hydrogen storage materials have gained great attention. For instance, the $Ti_{25}V_{35}Cr_{40}$ hydrogen storage alloy with the reversible hydrogen storage capacity of 1.8 wt. % at room temperature is larger than conventional $LaNi_5$ hydrogen storage alloy (1.2 wt. %). After adding 0.1% carbon, the hydrogen desorption pressure of $Ti_{25}V_{35}Cr_{40}$ is increased, thus enhancing the effective hydrogen desorption capacity at room temperature about 8-20%. As such, this kind of hydrogen storage alloy has a unique potential of commercialization and academic study.

The hydrogenation reaction of hydrogen storage material is accompanied by reactive heat. Since the hydrogenation is reversible, a lot of hydrogen gas can be stored, with an exothermic reaction during absorption and endothermic reaction during desorption. Hence, the utilization quality of hydrogen storage material is crucial to its absorption and desorption properties. However, irrespective of the performance of hydrogen storage material, ageing and degradation problems will be encountered over time. Said ageing and degradation phenomenon may be caused by intrinsic microstructure change of hydrogen storage material, or loss of absorption/desorption capability due to the surface covered by the extrinsic impurities in the hydrogen source. In the practice, these problems have to be characterized by specifically designed analyzers, therefore, the hydrogen storage material analyzer plays a decisive role in the development of high performance hydrogen storage material.

The existing hydrogen storage material analyzers are currently categorized into two types: $H_2$ absorption-desorption cycling testers, and temperature programmed desorption (TPD) spectrometers. The former one is intended for ageing test through cyclic hydrogen absorption-desorption, while the latter one is devoted to the dehydrogenation thermodynamics of hydrogen storage materials.

The above two hydrogen storage material analyzers along with their technologies are represented by different functions and significance. However, as these two instruments are operated separately, it is difficult to guarantee consistent analyses of hydrogen storage material, and in other words, the samples must be placed on the cyclic hydrogen absorption-desorption tester in the first phase, and then removed and shifted to TPD for analysis and test in the second phase. In such a case, this will lead to not only inefficient analysis, but also error arising from sample removal, thus affecting the final accuracy and quality of analysis and testing.

Thus, to overcome the aforementioned problems of the prior art, it would be an advancement if the current art can provide an improved design that can significantly increase the accuracy and efficacy of analysis and testing.

Therefore, the inventor has provided the present invention of practicability after deliberate experimentation and evaluation based on years of experience in the production, development and design of related products.

BRIEF SUMMARY OF THE INVENTION

Based on the unique configuration of the present invention wherein "the hydrogen storage material analyzer along with its analysis and activation methods" mainly comprises: a $H_2$ absorption-desorption cycling tester, a temperature-programmed desorption spectrometer, a specimen holder and a temperature-controlled furnace, a complete set of instruments can be used to implement simultaneously cycling desorption test, desorption analysis and activation requirements, thus eliminating the problem of removing the samples to another instrument for the intended purposes. Hence, the present invention presents better working efficiency, higher analysis accuracy and quality.

Although the invention has been explained in relation to its preferred embodiment, it is to be understood that many other possible modifications and variations can be made without departing from the spirit and scope of the invention as hereinafter claimed.

DETAILED DESCRIPTION OF THE INVENTION

Figure 1:
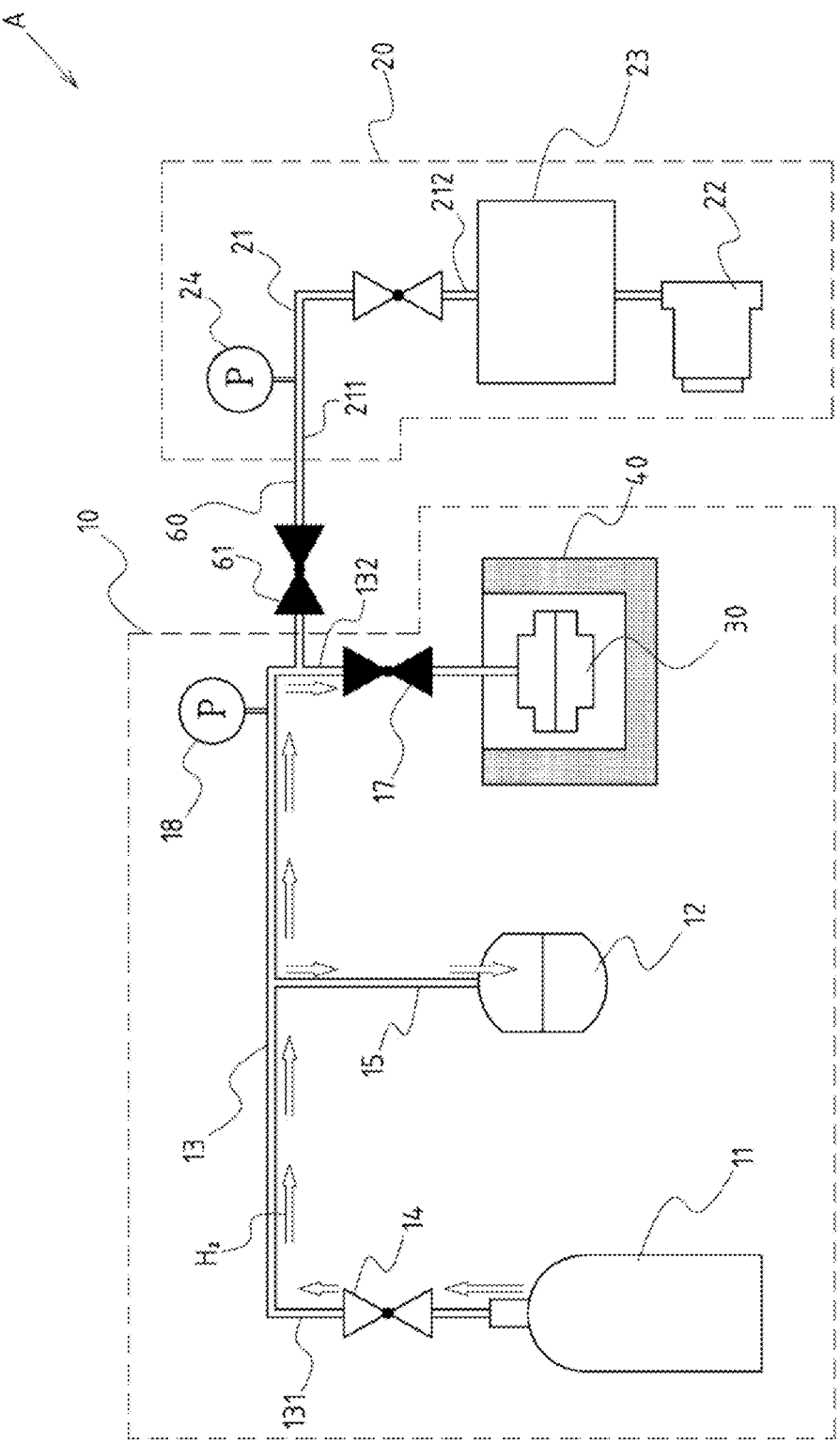
FIG. 1 is a schematic view of the hydrogen storage material analyzer of the present invention indicating hydrogen supply of the hydrogen cylinder.
Figure 2:
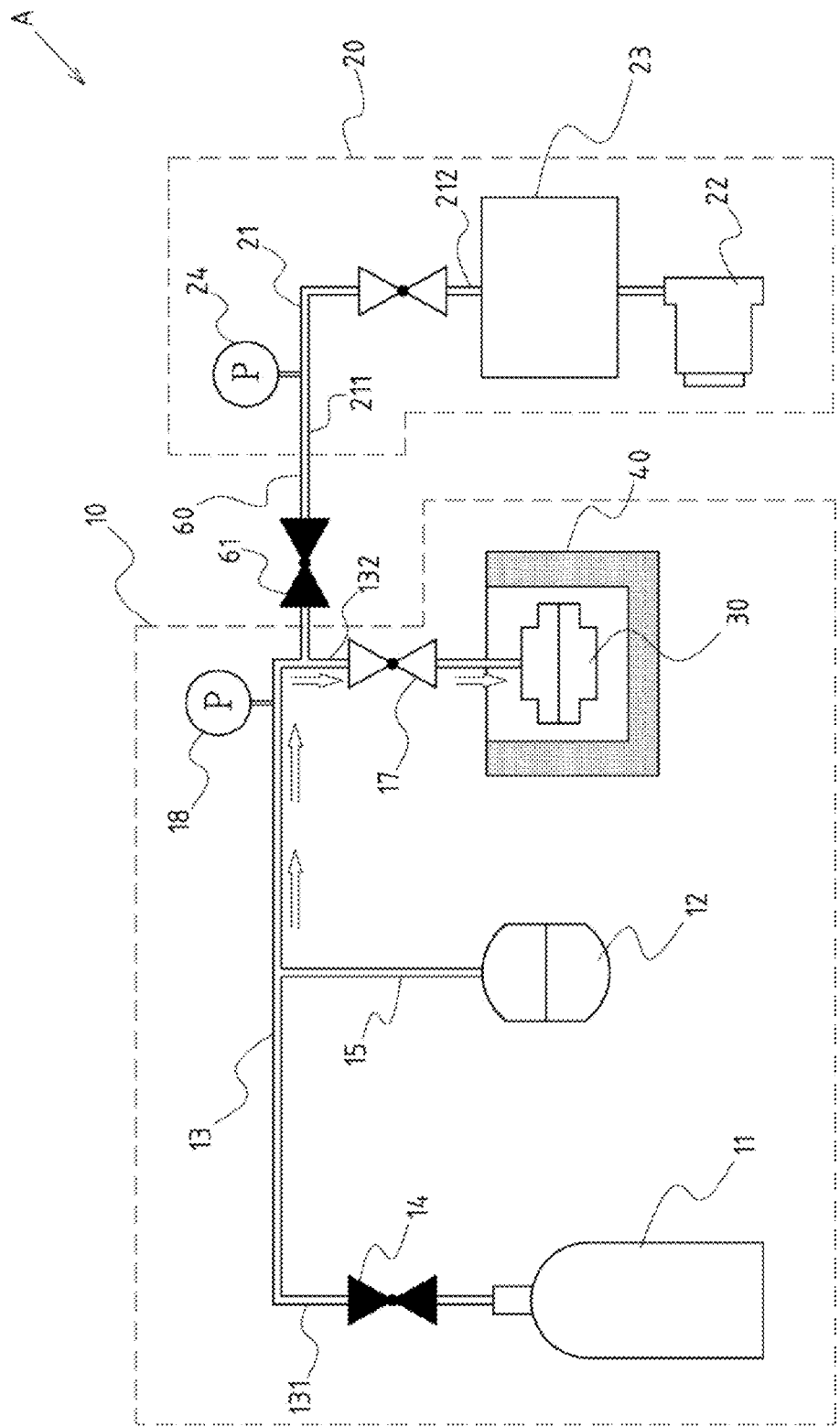
FIG. 2 is a schematic view of the present invention wherein the specimen valve is opened to guide hydrogen into the specimen holder.

FIGS. 1-2 depict preferred embodiments of a hydrogen storage material analyzer of the present invention along with analysis and activation method, which, however, are provided for only explanatory objective for patent claims.

Figure 3:
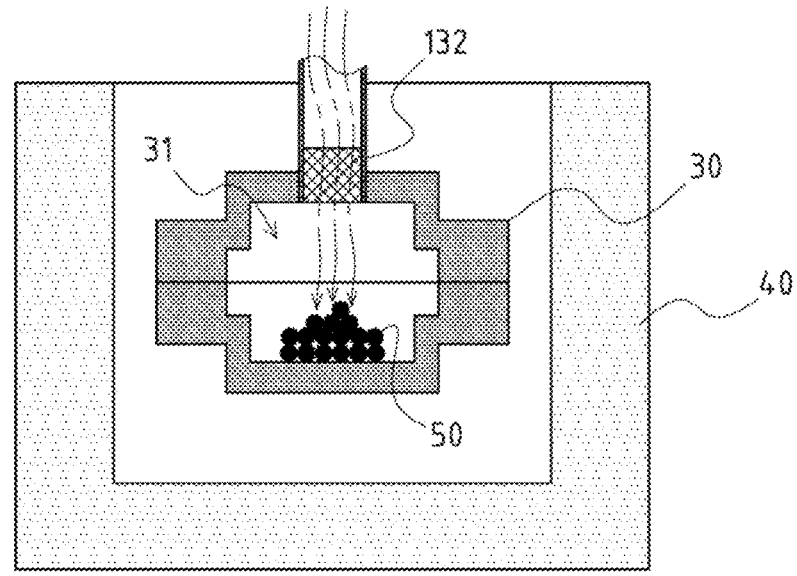
FIG. 3 is a sectional view of the specimen holder of the present invention indicating the hydrogen absorption state of the hydrogen storage material.
Figure 4:
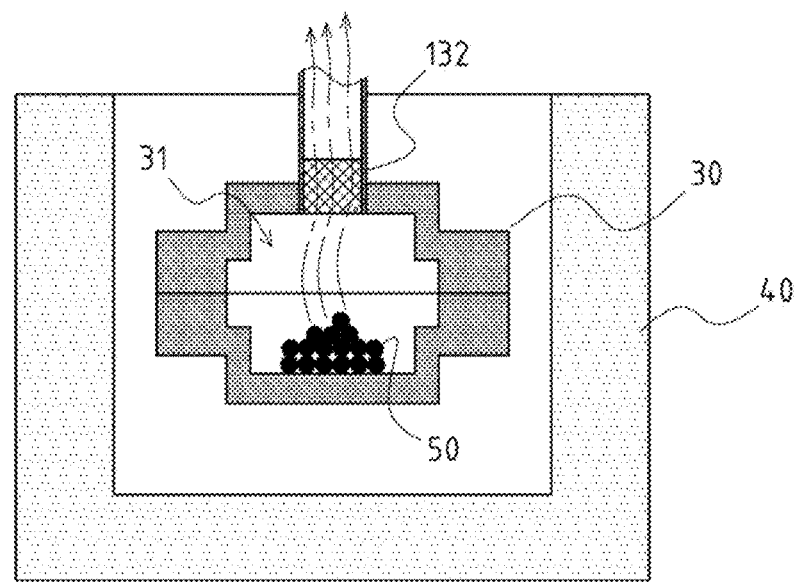
FIG. 4 is a schematic view of the hydrogen storage material with hydrogen desorption state of the present invention.

Said hydrogen storage material analyzer A comprising: a $H_2$ absorption-desorption cycling tester 10, a temperature-programmed desorption spectrometer 20, a specimen holder 30 and a temperature-controlled furnace 40. The specimen holder 30 is used to load the hydrogen storage material 50 (marked in FIGS. 3, 4).

The $H_2$ absorption-desorption cycling tester 10 includes a hydrogen cylinder 11, a hydrogen reservoir 12 and a hydrogen pipeline 13. The first end 131 of the hydrogen pipeline 13 is linked to the hydrogen cylinder 11, and the second end 132 of the hydrogen pipeline 13 is connected to the specimen holder 30. The first end 131 of the hydrogen pipeline 13 is fitted with an inlet valve 14 to control the on/off state of hydrogen supply from the hydrogen cylinder 11. The hydrogen reservoir 12 is linked to the hydrogen pipeline 13 via a bypass flow channel 15. The second end 132 of the hydrogen pipeline 13 is fitted with a specimen valve 17 to control the connection state between the hydrogen pipeline 13 and specimen holder 30. Moreover, a first pressure gauge 18 is arranged onto the hydrogen pipeline 13 between the specimen valve 17 and inlet valve 14.

The temperature-programmed desorption spectrometer 20 includes a hydrogen desorption channel 21, a vacuum pump 22 and a mass spectrometer 23. The hydrogen desorption channel 21 is provided with a first end 211 to link the second end 132 of the hydrogen pipeline 13 of the $H_2$ absorption-desorption cycling tester 10. The mass spectrometer 23 is linked to the second end 212 of the hydrogen desorption channel 21. The mass spectrometer 23 is set in front of the vacuum pump 22. A second pressure gauge 24 is arranged between the vacuum pump 22 and the first end 211 of the hydrogen desorption channel 21.

An integrated joint 60 is used to couple the second end 132 of the hydrogen pipeline 13 of the $H_2$ absorption-desorption cycling tester 10 with the first end 211 of the hydrogen desorption channel 21 of the temperature-programmed desorption spectrometer 20. Moreover, the integrated joint 60 is provided with a joint valve 61 to control the connection state of the hydrogen pipeline 13 and hydrogen desorption channel 21.

Furthermore, the temperature-controlled furnace 40 is used for temperature control of the specimen holder 30, while the specimen holder 30 is provided with a specimen space 31 (see FIG. 3) to load the hydrogen storage material 50.

Based on the above-specified structural configuration, the analysis and activation methods for the hydrogen storage material analyzer A are described below:

First, automatic cycling absorption and desorption methods of the present invention are briefed below:

The structural configuration of the hydrogen storage material analyzer A of the present invention is shown in FIG. 1, wherein the system framework is composed of electronic control unit, hydrogen pipeline and temperature-controlled furnace. Said electronic control unit comprises a personal computer, signal input/output interface card, relay control interface card and electromagnetic valve assembly. As for the hydrogen storage material analyzer A of the present invention, the cyclic absorption and desorption steps are described as follows:

a. The electromagnetic valve assembly is controlled by a program, and the electromagnetic valve is used to activate the working gas flow (5 kg/cm$^2$) to the designated actuator chamber of pneumatic valve, enabling automatic hydrogen charging and discharge for hydrogen storage material.

b. Take hydrogen-charging process as a example: the reaction temperature of the hydrogen storage material is controlled at a constant temperature (e.g.: 30 degrees C.). When the inlet valve 14 is opened by a computer, hydrogen $H_2$ starts to enter into the hydrogen reservoir 12 (see FIG. 1), and the pressure reading is sent back to the computer. When the $H_2$ pressure conforms to the setting value, the inlet valve 14 is shut down immediately (see FIG. 2, represented by blacking), then the specimen valve 17 is opened, allowing hydrogen $H_2$ to enter into the specimen holder 30, so that hydrogen storage material 50 (e.g.: hydrogen storage alloy) in the specimen holder 30 starts to absorb hydrogen (see FIG. 3).

c. When the pressure reading drops over time, the hydrogen storage material 50 starts to absorb hydrogen, during which the kinetics curve is recorded by the computer, and the hydrogen absorption of hydrogen storage material 50 (wt. %) is calculated by the pressure difference. After the absorption reaction is equilibrated, the joint valve 61 of the integrated joint 60 is opened to discharge hydrogen stored in the hydrogen storage alloy (see FIG. 4), thus finishing a cycle of absorption and desorption of hydrogen storage material 50.

Additionally, the cyclic hydrogenation-dehydrogenation performance of hydrogen storage material 50 can be measured and monitored by a program-controlled process.

Figure 6:
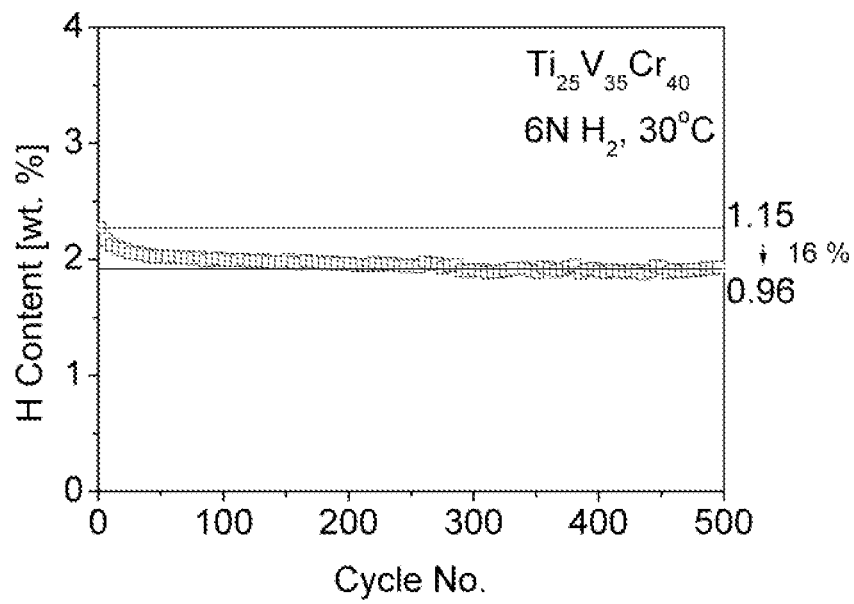
FIG. 6 is a cycling degradation curve of $Ti_{25}V_{35}Cr_{40}$ hydrogen storage material in a hydrogen test (purity 99.9999%).
Figure 7:
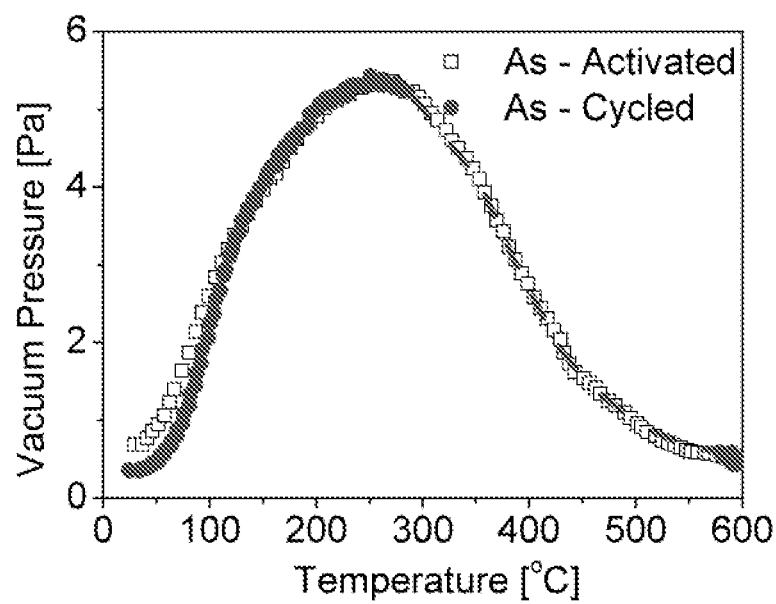
FIG. 7 is a comparison view of TPD spectra of $Ti_{25}V_{35}Cr_{40}$ hydrogen storage material before/after 500 cycles.

The analysis and activation methods of the hydrogen storage material of the present invention are described below:

1. Intrinsic hydrogenation degradation:

Through programmed operation of on/off for the valves in the $H_2$ absorption-desorption cycling tester 10 and temperature-programmed desorption spectrometer 20, hydrogenation degradation of $Ti_{25}V_{35}Cr_{40}$ hydrogen storage material are observed after 500 cycles of absorption and desorption using 6N hydrogen as shown in FIG. 6, the degradation is about 16.5%. The hydrogenation degradation mechanism of common alloy is divided into intrinsic and extrinsic degradation. To further analyze 16.5% hydrogenation degradation of $Ti_{25}V_{35}Cr_{40}$ hydrogen storage material, extrinsic degradation must be firstly considered; after 500 cycles of test, long-lasting dehydrogenation at room temperature is conducted, allowing the hydrogen storage material to be as β hydride within the specimen holder 30. The TPD spectrum in this state is shown in FIG. 7, wherein the TPD curve of β hydride before/after cycling differs little, thus demonstrating that the extrinsic factors to degrade hydrogen storage material are eliminated.

Figure 8:
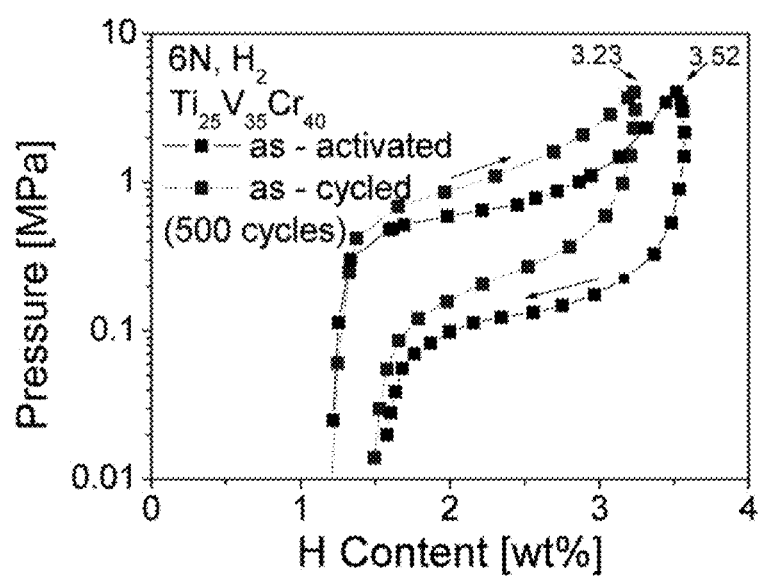
FIG. 8 is a PCI curve of $Ti_{25}V_{35}Cr_{40}$ hydrogen storage material before/after 500 cycles.
Figure 9:
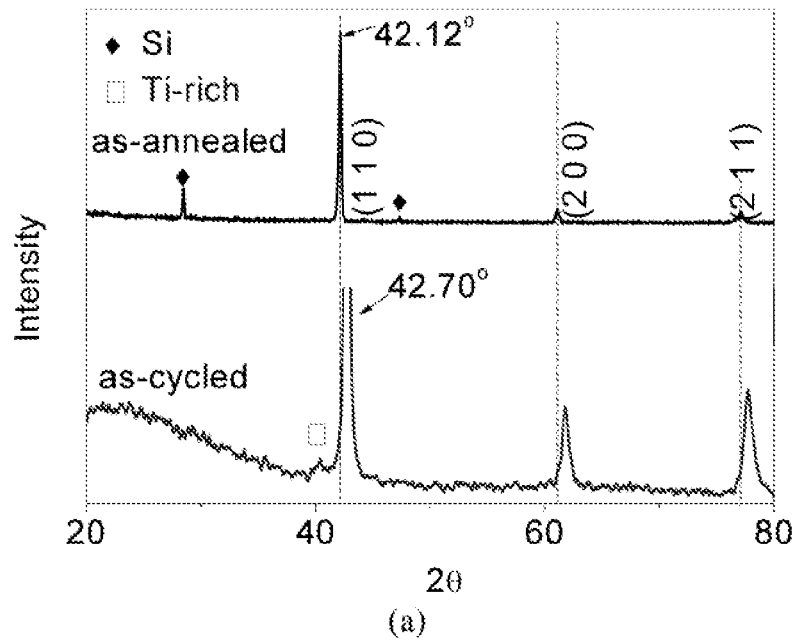
FIG. 9(a) shows a XRD diffraction pattern of $Ti_{25}V_{35}Cr_{40}$ hydrogen storage material before/after 500 cycles.
FIG. 9(b) show peaks for Ti-rich precipitate tested in a slow diffraction mode (lo/min).
Figure 9:
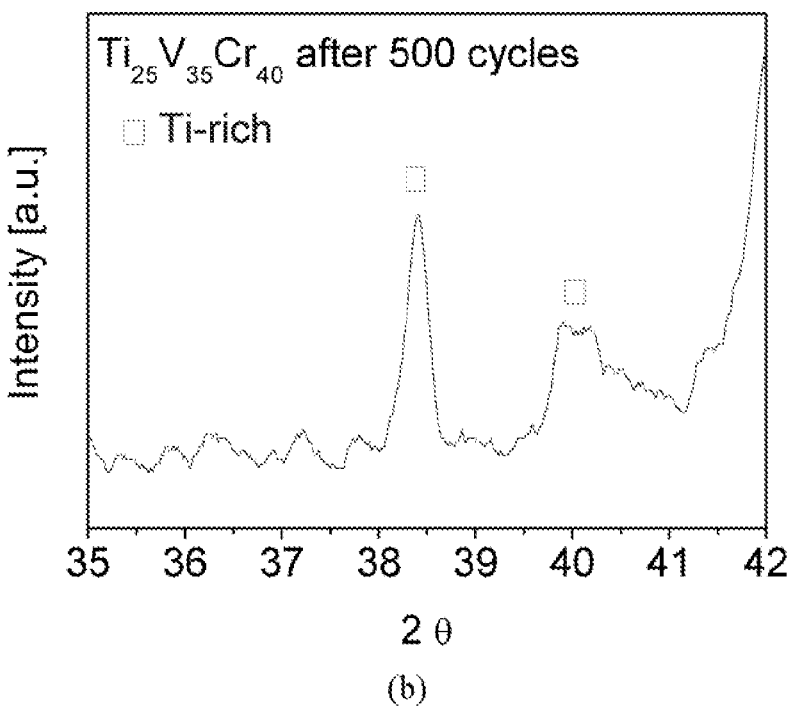

Hydrogenation degradation of $Ti_{25}V_{35}Cr_{40}$ hydrogen storage material after 500 cycles of test is caused by intrinsic factors as indicated by the variation of PCI (Pressure-Composition-Isotherm) curve in FIG. 8. Maximum hydrogen absorption of hydrogen storage material drops from 3.52 wt. % to 3.23 wt. %, with a degradation about 8.2%, and the hydrogen pressure within the specimen holder 30 rises. Besides, it is found from XRD diffraction experiment that (see FIG. 9), for the hydrogen storage material after 500 cycles of test, the diffraction angle shifts towards a higher angle, showing the reduction of lattice constant, and accounting for the rising flat pressure of absorption. Meanwhile, minor diffraction peak (see FIG. 9) occurs nearby 2θ=38.5° and 40°, and is assigned as Ti-rich precipitate. As the radius of titanium, vanadium and chrome is 0.145, 0.132 and 0.125 nm, respectively, the formation of this precipitate will lead to reduction of both titanium concentration within $Ti_{25}V_{35}Cr_{40}$ matrix and $Ti_{25}V_{35}Cr_{40}$ lattice constant.

Figure 10:
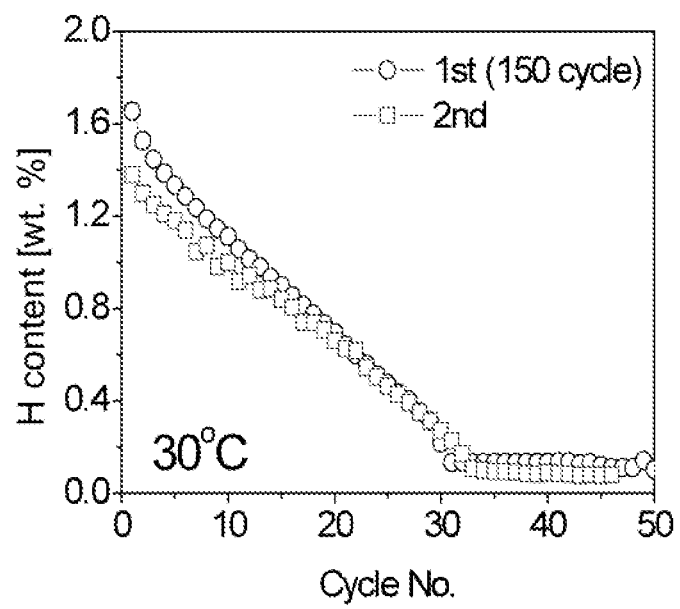
FIG. 10 shows hydrogenation degradation curves of the hydrogen storage material of the present invention (purity 99.99%).

2. Extrinsic hydrogenation degradation:

Extrinsic hydrogenation degradation is tested by taking 5N hydrogen as gas source or by adding toxic microelement CO, $H_2S$, $CO_2$, $H_2O$, etc, and then the degradation of $Ti_{25}V_{35}Cr_{40}$ alloy reacting with hydrogen source of lower purity is observed. The resulting findings are shown in FIG. 10, wherein after 33 cycles of tests, serious hydrogenation degradation of $Ti_{25}V_{35}Cr_{40}$ hydrogen storage material occurs (down from 1.6 wt. % to 0 wt. %).

Figure 11:
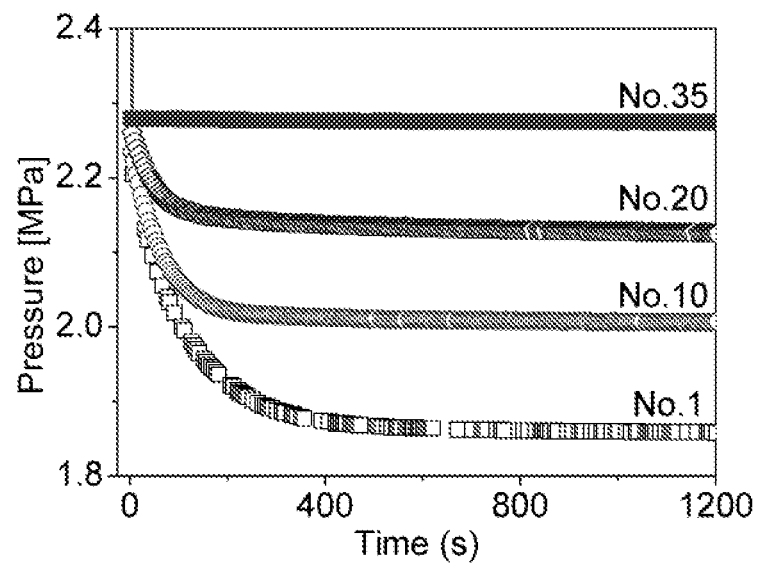
FIG. 11(a) shows variation of hydrogen absorption pressures of the hydrogen storage material during the cycles.
FIG. 11(b) shows hydrogen desorption pressure of the hydrogen storage material during the cycles.
Figure 11:
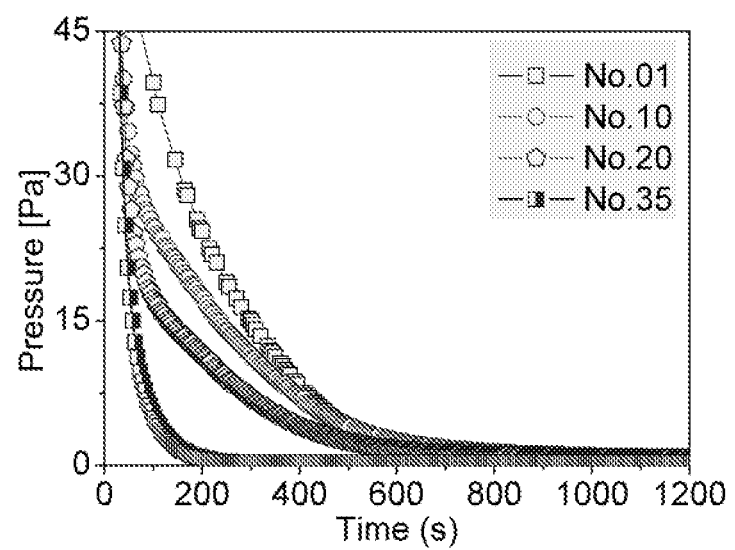
Figure 12:
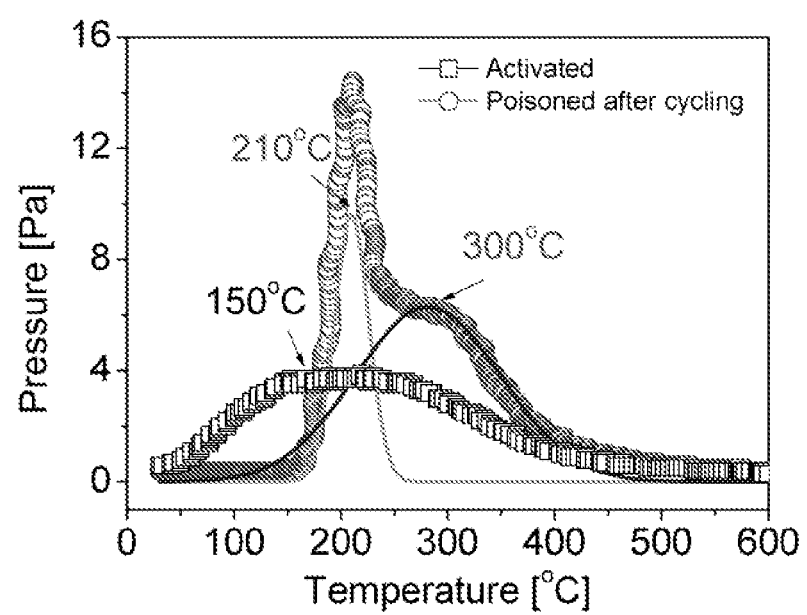
FIG. 12 shows a TPD spectra between activated and poisoned alloys after 150 cycles.

To understand the reason of degradation, the cycling hydrogenation properties including the hydrogen absorption/desorption pressure as function of cycle are monitored shown in FIG. 11. It is found that, the hydrogen absorption stops gradually over time, showing that serious degradation of hydrogen storage material occurs or hydrogen desorption is disabled due to obstruction. On the other hand, as shown in FIG. 12, it is observed from degraded alloy's TPD spectrum (TPD spectrum is generated by the second pressure gauge 24 of temperature-programmed desorption spectrometer 20) that, there is not any dehydrogenation signal from room temperature to 160° C., but there are two dehydrogenation peaks at about 210° C. and 300° C., representing dehydrogenation of titanium alloy's δ→β and β→α hydride. As the former one's, appropriate dehydrogenation temperature is room temperature and it can be seen that poisoning of hydrogen storage alloy may occur in such case. Thus, loss of hydrogen absorption/desorption capability is attributed to the surface of hydrogen storage material covered by impurities in the hydrogen source. Moreover, it is proved that dehydrogenation temperature of poisoned $Ti_{25}V_{35}Cr_{40}$ is 160° C. Hence, re-activation temperature of poisoned hydrogen storage material should be set above this temperature.

Figure 13:
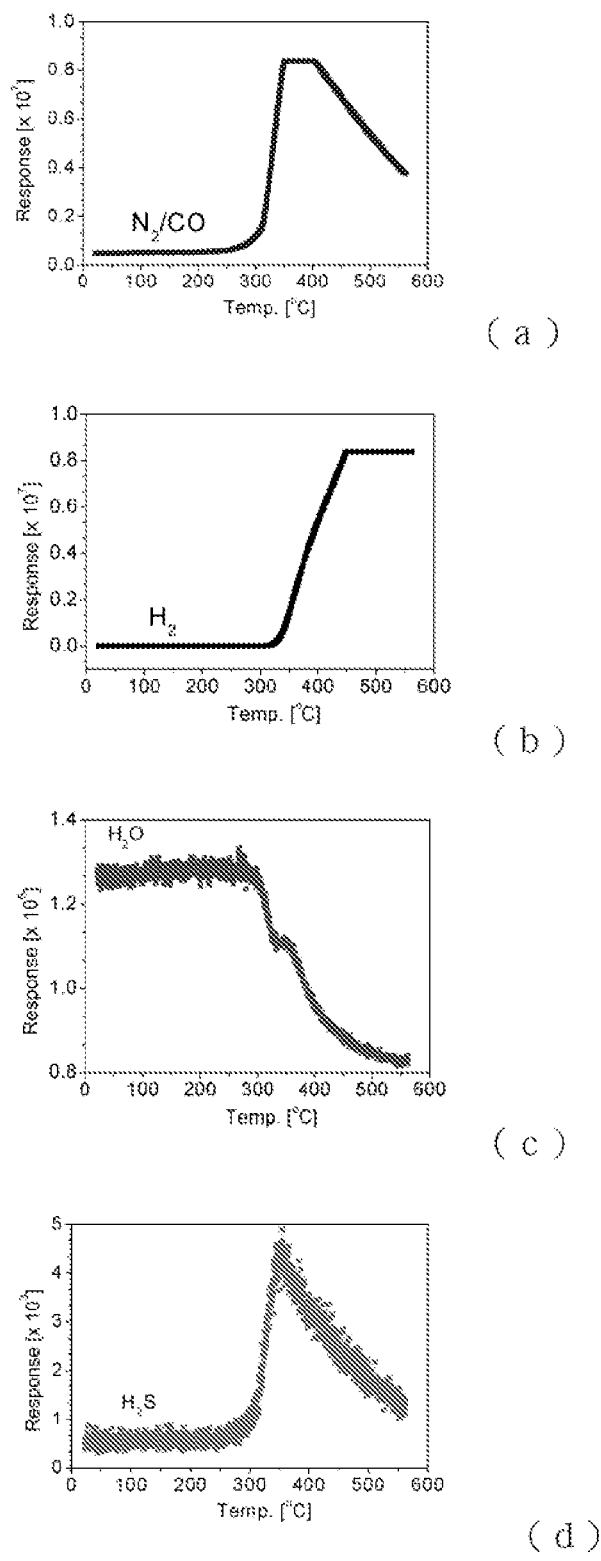
FIG. 13(a) shows TPD-MS spectra of poisoned alloys for $N_2/CO$.
FIG. 13(b) shows TPD-MS spectra of poisoned alloys for $H_2$.
FIG. 13(c) shows TPD-MS spectra of poisoned alloys for $H_2O$.
FIG. 13(d) shows TPD-MS spectra of poisoned alloys for $H_2S$.
Figure 14:
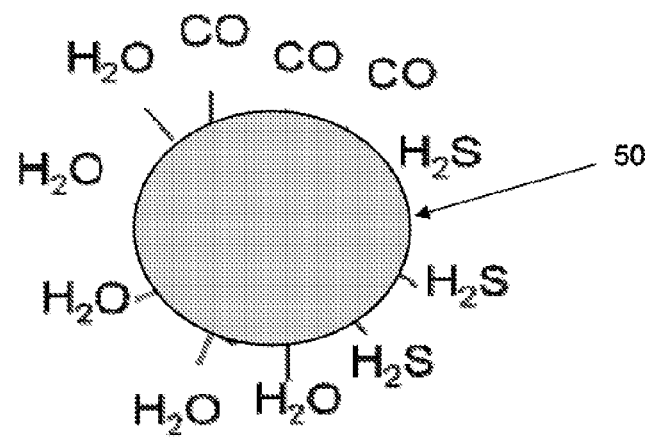
FIG. 14 is a schematic view of extrinsic hydrogenation degradation of hydrogen storage material in the present invention.
Figure 15:
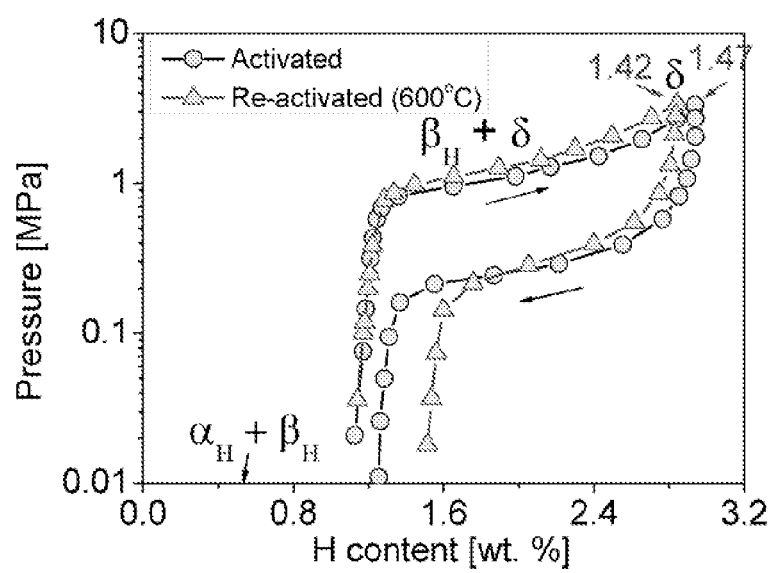
FIG. 15 shows a comparison of PCI curves of hydrogen storage material in the condition of activated and re-activated in the present invention.

Toxic substance is originated from impurities from hydrogen source, impeding the formation of hydride by reacting hydrogen with alloy. Referring also to FIG. 13, it is found from TPD-MS spectra (this signal is generated by mass spectrometer of temperature-programmed desorption spectrometer), with the temperature rise of hydrogen storage material, some substances, such as: $H_2$, $H_2O$, CO, $O_2$ and $H_2S$, are desorbed from the surface. It is clear that hydrogenation poisoning of hydrogen storage material is caused from the alloy surface covered by toxic substance (see FIG. 14), thus reducing greatly the hydrogenation capability of hydrogen storage material. Meanwhile, dissociation temperature of TPD-MS spectra is defined as the dehydrogenation temperature of poisoned hydrogen storage material, and re-activation temperature of poisoned hydrogen storage material will be above this temperature. After temperature programmed dehydrogenation, a PCI curve (see FIG. 15) of the degraded hydrogen storage material is observed, showing that the flat pressure and maximum absorption, etc, are the same with original alloy. Thus, it is judged that hydrogenation degradation of the hydrogen storage material is not derived from the change of microstructure.

Figure 5:
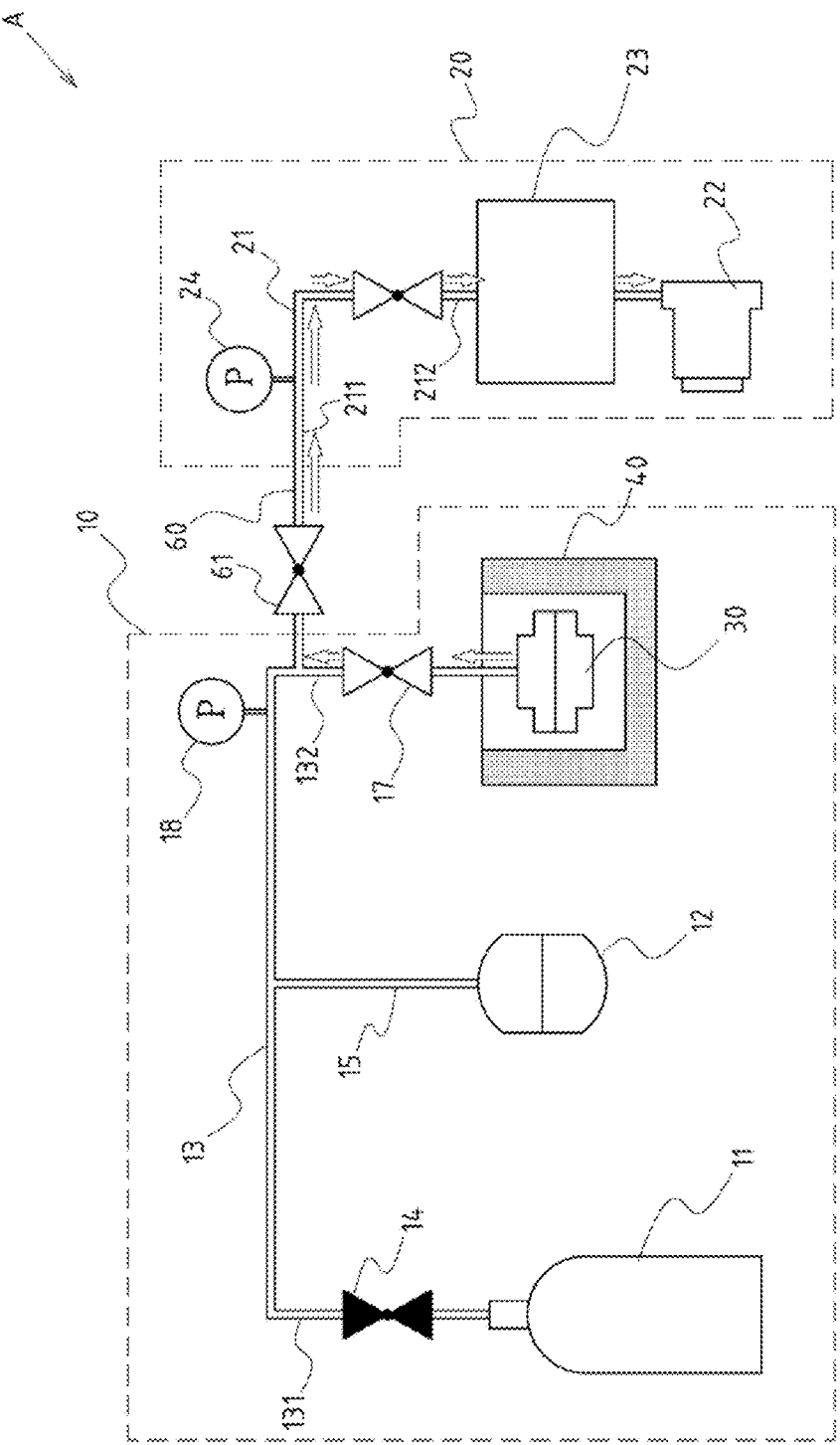
FIG. 5 is a schematic view of the present invention wherein the mass spectrometer is used for desorption analysis of the hydrogen storage material.

3. Re-activation of hydrogen storage material: (see FIG. 5)

After extrinsic hydrogenation degradation of the hydrogen storage material is confirmed, it is required to shut down the inlet valve 14 for the first end 131 of the hydrogen pipeline 13, and open the joint valve 61 for the first end 211 of the hydrogen desorption channel 21, then start the temperature-controlled furnace 40 to heat up the specimen holder 30. Moreover, the heating temperature is controlled over a dehydrogenation temperature, e.g.: 160° C., so as to dispel toxic substances covered on the surface of the hydrogen storage material. Next, the vacuum pump 22 of the temperature-programmed desorption spectrometer 20 is started to discharge the toxic substances for reactivation of the hydrogen storage material.

We claim:

1. A method for examining extrinsic hydrogenation degradation by using a hydrogen storage material analyzer, a hydrogen absorption-desorption cycling tester and a temperature-programmed desorption spectrometer equipped with a mass spectrometer and a specimen holder and a temperature-controlled furnace, the method comprising:

testing a degradation of the hydrogen storage material in the specimen holder by using a lower purity hydrogen gas or by adding toxic molecules selected from the group consisting of CO, $H_2S$, $CO_2$, $H_2O$, and $H_2$ gas, the hydrogen storage material being a metal alloy;

conducting a cycling of hydrogen absorption and desorption of the hydrogen storage material such that hydrogen pressure for absorption and desorption stops gradually over time;

obtaining a hydrogenation degradation property so as to show that significant degradation of the hydrogen storage material has occurred or that desorption is disabled due to an extrinsic obstruction;

obtaining dehydrogenation temperature of the cycled hydrogen storage material from a spectrum produced by the temperature-programmed desorption spectrometer so as to verify whether a loss of hydrogen storage in the hydrogen storage material is caused by extrinsic poisoning on a surface of the hydrogen storage materials;

measuring a temperature-programmed desorption and mass curve of hydrogen storage materials by the mass spectrometer so as to examine types and amounts of impurities desorbed from the degraded hydrogen storage material and to characterize an adsorption strength of the impurities with the cycled hydrogen storage materials so as to provide a basis for developing a high-performance hydrogen storage material against extrinsic hydrogenation degradation; and applying a temperature-programmed dehydrogenation treatment to the degraded hydrogen storage materials so as to obtain flat pressure and maximum absorption properties of the degraded hydrogen storage material in a PCI curve so as to show that the hydrogenation degradation of the hydrogen storage material is not derived from a change of microstructure.

2. The method of claim 1, the hydrogen storage material analyzer has a hydrogen pipeline with an inlet valve and a hydrogen desorption channel with a joint valve, the temperature-programmed desorption spectrometer has a vacuum pump, and wherein the method further comprising after verification that the hydrogenation degradation has resulted from extrinsic factors:

closing the inlet valve of the hydrogen pipeline;
opening the joint valve of the hydrogen desorption channel;
restarting the temperature-controlled furnace so as to heat the specimen holder;
setting a temperature of the temperature-controlled furnace to the dehydrogenation temperature; and
starting the vacuum pump of the temperature-programmed desorption spectrometer so as to discharge toxic substances absorbed on the hydrogen storage material for re-activation purposes.

* * * * *